United States Patent [19]

Zhu et al.

[11] Patent Number: 5,089,111
[45] Date of Patent: Feb. 18, 1992

[54] ELECTROPHORETIC SIEVING IN GEL-FREE MEDIA WITH DISSOLVED POLYMERS

[75] Inventors: Ming D. Zhu, Berkeley; Jeng-Chyh Chen, Alameda, both of Calif.; Stellan Hjerten, Upsala, Sweden

[73] Assignee: Bio-Rad Laboratories, Inc., Hercules, Calif.

[21] Appl. No.: 589,915

[22] Filed: Sep. 27, 1990

Related U.S. Application Data

[63] Continuation-in-part of Ser. No. 303,174, Jan. 27, 1989, abandoned.

[51] Int. Cl.$^5$ ............... G01N 27/26; B01D 57/02
[52] U.S. Cl. ............... 204/180.1; 204/299 R
[58] Field of Search ............... 204/299 R, 180.1

[56] References Cited

U.S. PATENT DOCUMENTS 4,305,798  12/1981  Cunningham et al. ............... 204/180

OTHER PUBLICATIONS

Hjerten, S. et al, "High-Performance Electrophoresis of Acid and Basic Low-Molecular-Weight Compounds and of Proteins in the Presence of Polymers and Neutral Surfactants", Journal of Liquid Chromatography, 12(13), 2471-2499 (1989).

Tietz, Dietmar et al, "Electrophoresis of Uncrosslinked Polyacrylamide: Molecular Sieving and Its Potential Applications", Electrophoresis 7, 217-220 (1986).

*Primary Examiner*—John Niebling
*Assistant Examiner*—John S. Starsiak, Jr.
*Attorney, Agent, or Firm*—Townsend and Townsend

[57] ABSTRACT

Separation of sample ions on the basis of molecular size is achieved by electrophoresis in an aqueous solution containing a dissolved non-crosslinked polymer. The polymer has a molecular weight range which overlaps that of the sample ions being separated. Species which vary in molecular weight but not in charge/mass ratio are separated by this method, which is of particular interest in high performance electrophoresis in capillary columns where the use of gels would be awkward and inconvenient.

19 Claims, No Drawings

ELECTROPHORETIC SIEVING IN GEL-FREE MEDIA WITH DISSOLVED POLYMERS

CROSS REFERENCE TO RELATED APPLICATION

This application is a continuation-in-part of copending application Ser. No. 07/303,174, filed Jan. 27, 1989, now abandoned.

This invention relates to electrophoretic separations, and to separations of species in a sample based on molecular size.

BACKGROUND OF THE INVENTION

Molecular sieve electrophoresis is a powerful method for separating macromolecular solutes both among themselves with high resolution on the basis of molecular size and from solutes of lesser molecular size. The gel media in which these separations take place however require careful preparation and special handling techniques, with problems in reproducibility and stability.

Capillary free zone electrophoresis, on the other hand, is also of interest for certain types of separations, since it permits the use of high voltages which provide the advantage of relatively high speed. The small size of the capillary further permits the separation of extremely small samples in a buffer solution without the use of complex media such as a gel or paper, and with relatively little band broadening. Capillary free zone electrophoresis is particularly useful in the separation of small peptides and proteins. Separation occurs on the basis of the charge/mass ratio, however, and for this reason certain separations are very difficult to achieve by this method, notably those involving high molecular weight polynucleotides and many SDS-treated proteins.

Gel media may be placed in capillaries for molecular sieve separations, but the preparation and use of such gels is particularly problematic, since they undergo physical and chemical changes with each use and thus for practical purposes can only be used once. This is detrimental to the reproducibility of the separations and to the efficiency of the technique. In addition, it raises serious problems for those capillaries which are incorporated into cartridges designed for automated instrumentation.

SUMMARY OF THE INVENTION

It has now been discovered that sample ions, and particularly biomolecules, may be separated from each other on the basis of molecular size by electrophoresis through an aqueous solution of a non-crosslinked polymer of a selected molecular weight (or molecular weight range) and concentration. The molecular weight of the polymer will be selected as described below to correspond to the molecular weight range of the sample ions in a manner which will inhibit the migration of the sample ions through the solution to varying degrees. Macromolecular sample ions and other biological species may thus be separated from each other and from sample ions of lesser size without the use of a gel. The terms "macromolecule" and "macromolecular" are used herein to refer to species having molecular weights of at least about 10,000.

The polymers used herein are generally non-crosslinked polymers. Branched or linear polymers may be used, linear polymers being preferred for many applications. In addition, the polymers may be neutral or charged, neutral being preferred in applications where charge interaction between the sample ions and the polymer is sought to be avoided.

Cellulose derivatives have been used in capillary electrophoresis for suppressing electroendosmosis and other types of bulk flow by increasing the viscosity of the buffer solution, and for preserving the capillary as well. The quantities used for this purpose are small, however, with no substantial tendency to detain the sample ions during their migration or to affect their separation. The present invention resides in the discovery that dissolved linear polymers in general produce a molecular sieving effect when used in certain amounts, these amounts being generally higher than the amounts of the cellulose derivatives used for suppressing bulk flow.

Aqueous media with dissolved polymers in accordance with this invention may be used for biomolecular separations in general, although they are of particular utility in separations performed in capillary columns with high voltage, i.e., high performance electrophoresis. The use of polymers in this manner permits the separation of species which vary in molecular weight with insufficient or no variation in charge/mass ratio, and lends itself to easy preparation of the separation media and high reproducibility.

As in the known use of cellulose derivatives referred to above, the dissolved polymers further serve to suppress bulk flow due to their inherent increase in viscosity. Examples of bulk flow occurring spontaneously are electroendosmosis, hydrokinetic flows (due to hydrostatic heads), and convection. At these polymer levels, however, the decrease in sample ion mobility caused by the presence of the polymers varies both with the size and concentration of the polymer and the size of the sample ion, a feature which does not occur at the low levels at which the cellulose derivatives have been used for suppressing bulk flow.

Other features and advantages of the invention will be apparent from the description which follows.

DETAILED DESCRIPTION OF THE INVENTION AND PREFERRED EMBODIMENTS

The polymers used in connection with the present invention must be water-soluble and, as stated above, are preferably linear.

Selection of the polymer is optimally geared toward the particular sample ions being separated. The molecular weight of the polymer is of primary interest in making this selection. In general, polymers varying widely in molecular weight may be used. Resolution of the sample ions will generally improve, however, as the polymer molecular weight approaches the range of the molecular weights of the sample ions. The best results are obtained with polymers having an average molecular weight which is between the lowest and highest molecular weights of the sample ions, and in particular with polymers whose molecular weight range covers (i.e., is at least coextensive with) the molecular weight range of the sample ions. In preferred embodiments, the polymer has an average molecular weight which is from about 10,000 to about 2,000,000, and within about 0.1 to about 200 times, more preferably from about 0.2 to about 20 times, and most preferably from about 0.5 to about 2 times the average molecular weight of the sample ions.

Within these parameters, the particular type of polymer may vary widely. For aqueous systems, examples of polymers which may be used are water-soluble cellulose derivatives, fully water-soluble polyalkylene glycols, water-soluble saccharide-based and substituted saccharide-based polymers, water-soluble polysilanes, polyvinylalcohol and polyvinylpyrrolidone.

Specific examples of water-soluble cellulose derivatives useful in this invention are sodium carboxymethyl cellulose, sodium carboxymethyl 2-hydroxyethyl cellulose, 2-hydroxyethyl cellulose, 2-hydroxypropyl cellulose, methyl cellulose, hydroxypropyl methyl cellulose, hydroxyethyl methyl cellulose, hydroxybutyl methyl cellulose, and hydroxyethyl ethyl cellulose. Preferred cellulose derivatives are those with a highly hydrophilic character, and consequently high water solubility and minimal affinity to the sample ions. Methyl cellulose is particularly preferred. Celluloses are generally characterized in terms of the viscosity of aqueous solutions in which they are dissolved at specified concentrations and temperature. With this in mind, and depending on the size of the sample ions sought to be separated, the cellulose derivative may vary widely in terms of this viscosity characterization. For example, cellulose derivatives may be used which are characterized as producing viscosities ranging from about 15 centipoise to about 17,000 centipoise when dissolved in water at 2 weight percent measured at 25° C., although in the context of this invention they would be used at other concentrations. Polymers such as these are useful in separating polynucleotides with chains ranging from about 10 to about 10,000 base pairs. Preferred cellulose derivatives for use in the present invention are those which would have viscosities of from about 1,000 to about 10,000 centipoise if prepared as 2% aqueous solutions measured at 25° C. It is to be understood that these viscosity characterizations are intended merely as an indication of the molecular weight of the polymer, and not of the actual viscosity when used in the context of the present invention.

Preferred polyalkylene glycols are polyethylene glycols having average molecular weights of at least about 10,000. Particularly preferred are polyethylene glycols with average molecular weights of at least about 20,000, most preferably at least about 30,000. As an example, mixtures of sample ions ranging in molecular weight from about 10,000 to about 100,000 may be separated with polyethylene glycols ranging in molecular weight from about 10,000 to about 100,000.

Examples of saccharide-based and substituted saccharide-based polymers, both linear and branched, which are useful in the invention are dextran, hyaluronic acid (a polymer of acetylglucosamine and glu-curonic acid as alternating units), locust-bean gum (a polysaccharide plant mucilage which is essentially galactomannan), Polytran (a scleroglucan available from Pillsbury Co., Minneapolis, Minn.), Pustulan (a polysaccharide available from Calbiochem Corp., San Diego, Calif.), carrageenan (a charged polysaccharide), guar gum (a neutral polysaccharide), pectin (apolyuronide consisting chiefly of partially methoxylated galactouronic acids joined in long chains), amylose, amylopectin, soluble starch and hydroxylpropyl starch.

Mixtures of polymers in which varying molecular weights are purposely combined may also be used. This will be particularly useful in separating sample mixtures which have a wide range of molecular weights, thus providing separation over the entire range.

The use of charged polymers is an option which can provide a further separation parameter to the system. This will vary the interaction between the species and the polymer, and may thus be of use depending on the particular mixture of species present in the sample, and the type of separation sought among these species.

The quantity of polymer to be dissolved in the resolving solution may vary widely, and will be any quantity which extends the retention time of the sample ions to such varying degrees that effective separation on the basis of molecular size is achieved. Clearly, this will vary with various parameters of the system, including for example the column configuration and length, the presence and effect of other factors influencing the separation such as charge and electrophoretic mobility, the molecular structure, intrinsic viscosity and interactive character of the polymer itself, and the range of and differences between the molecular weights of the sample ions. The degree to which the retention times for the sample ions should be extended for best results will vary with the sample composition and the polymer being used. For separations of macromolecular species, increases in retention time of at least about 25%, preferably at least about 35%, and most preferably at least about 50%, will provide the best results. For polyalkylene glycols, particularly polyethylene glycols, concentrations of at least about 2% by weight, preferably at least about 3%, and most preferably from about 3% to about 30% by weight will give the best results. For cellulose derivatives and other types of polymers, preferred concentrations are at least about 0.1% by weight, with about 0.1% to about 30% by weight more preferred, and about 0.1% to about 10% by weight particularly preferred.

To conduct the separations in accordance with the present invention, operating conditions and procedures used in conventional electrophoretic separations, including appropriately selected buffer systems, may be used. The invention is of particular utility in high performance electrophoresis as performed in capillaries. Preferred capillaries are those having internal diameters of less than about 200 microns, more preferably less than about 100 microns, and most preferably about 25 microns to about 50 microns. Voltages of at least about 100 volts per centimeter length of the capillary are preferred, with at least about 200 volts/cm particularly preferred, and at least about 300 volts/cm most preferred.

The following examples are offered strictly for purposes of illustration, and are intended neither to define nor to limit the invention in any manner.

In each of these examples, electrophoresis was performed on an HPE-100 high performance electrophoresis instrument, a product of Bio-Rad Laboratories, Inc., Hercules, Calif. Capillary tubes of 20 cm length by 25$\mu$ inner diameter, and 50 cm length by 50$\mu$ inner diameter, coated with linear polyacrylamide as described in Hjertén, U.S. Pat. No. 4,680,201, issued July 14, 1987, were used. A conductivity bridge Model 31 from Yellow Springs Instrument Co., Yellow Springs, Ohio, was used, and detection was performed on-line in the capillary itself, by UV absorption. The hydroxypropyl methyl cellulose was obtained from Sigma Chemical Co., St. Louis, Mo., in powder form, specified in terms of its viscosity when prepared as an aqueous solution at a concentration of 2% by weight and measured at 25° C.

The specified viscosities were 15, 50, 100 and 4000 centipoise, and the powdered polymer will be referred to herein for convenience as "15-centipoise," "50-centipoise," "100-centipoise," and "4000-centipoise hydroxypropyl methyl cellulose." The 4000-centipoise hydroxypropyl methyl cellulose was estimated to have an average molecular weight of approximately 900,000. The methyl cellulose was also obtained from Sigma Chemical Co., similarly specified as producing a viscosity of 4000 centipoise in a 2% aqueous solution at 25° C., and will be referred to herein in a manner similar to the hydroxypropyl methyl cellulose. Dextran at molecular weights of 67,000, 162,000 and 485,000 was obtained from Sigma Chemical Co. Polyvinyl alcohol at a molecular weight of 50,000 was obtained from Aldrich Chemical Co., Inc.

The myoglobin was Type III from horse heart, and the albumin was Fraction V bovine serum albumin. The myoglobin, albumin and the substance P were also obtained from Sigma Chemical Co. The human carbonic anhydrase was obtained from Sigma Chemical Co. The DNA fragments used in Example 4 were a mixture used as Low Range Size Standards supplied by Bio-Rad Laboratories, Hercules, Calif., and included fragments containing 88, 222, 249, 279, 303, 634, 800, 1434 and 1746 base pairs. The lactoferrin used in Example 9 was obtained in purified form as a gift from Labofina (Belgium).

EXAMPLE 1

This example demonstrates the effect of polyethylene glycol (PEG) as a solute in an electrophoretic medium used for separating myoglobin and substance P. The first part of this example serves as a control test performed in the absence of the PEG, while the second shows the effect which the PEG has on the component separation.

A. Electrophoresis without sieve-promoting polymer

A sample solution was prepared by dissolving substance P and myoglobin in 10 mM pH 2.5 phosphate buffer to achieve concentrations of 100 $\mu$g/mL of substance P and 50 $\mu$g/mL of myoglobin. A sample less than 3 $\mu$L in volume of the solution was loaded electrophoretically on a coated 20 cm = 25$\mu$ capillary cartridge filled with the buffer solution. Electrophoresis was performed on the loaded sample by applying a potential of 8000 V across the capillary, with detection at 200 nm with a sensitivity range of 0.02 AUF.

The myoglobin eluted at a retention time of 2.8 minutes, and the substance P at 3.3 minutes. Note that the myoglobin migrated through the capillary faster than the substance P.

Electrophoresis in presence of PEG.

The experiment of Part A was repeated, the only difference being that the buffer solution in the capillary further contained PEG with an average molecular weight of approximately 35,000 at a concentration of 5 weight percent.

The sample components eluted in a reversed elution order and with lengthened retention times. The substance P eluted first at 4.9 minutes, followed by the myoglobin at 5.9 minutes.

EXAMPLE 2

This example illustrates the use of PEG in the electrophoretic separation of the monomer, dimer and trimer of albumin. The first part of this example is a control test, while the second includes the use of PEG.

A. Electrophoresis without sieve-promoting polymer

A sample was prepared by dissolving albumin as a mixture of the monomer, dimer and trimer in 10 mM pH 2.5 phosphate buffer to a total albumin concentration of 100 $\mu$g/mL. The sample was loaded, run and detected on the same column using the same conditions as in Example 1A. The result was a single sharp peak at a retention time of 3.5 minutes.

B. Electrophoresis in presence of PEG.

The experiment of Part A was repeated with the inclusion of PEG with an average molecular weight of approximately 35,000 at a concentration of 5 weight percent in the column solution. Monomer, dimer and trimer formed separate peaks at retention times of 5.6 minutes, 6.8 minutes and 7.7 minutes, respectively.

EXAMPLE 3

This example illustrates several conditions where water-soluble polymers were in the buffer solution but incomplete or no separation occurred due to insufficient amounts of polymer or due to polymer chains of insufficient length.

A. Albumin with 2% PEG of molecular weight 35,000

The experiment of Example 2B was repeated, using 2% of the PEG rather than 5%. The monomer was detected at a retention time of 3.7 minutes, and the dimer at 4.0 minutes, with the trimer peak not distinguishable. The monomer and dimer peaks overlapped.

Albumin with 5% PEG of molecular weight 6000

The experiment of Example 2B was repeated, using PEG of an average molecular weight of 6000 rather than 35,000. All of the albumin components passed the detector as a single peak at a retention time of 4.3 minutes, with no separation among the three.

C. Albumin and myoglobin/substance P with 0.25% 4000-centipoise hydroxypropyl methyl cellulose A solution was prepared by dissolving 4000-centipoise hydroxypropyl methyl cellulose in 0.1 M pH 2.5 phosphate buffer at 0.25 weight percent. The experiment of Example 2B (albumin sample) was then repeated, followed by the experiment of Example 1B (sample containing myoglobin and substance P), using this hydroxypropyl methyl cellulose-containing buffer solution in place of the PEG-containing buffer solution in the capillary in each case.

The monomer, dimer and trimer components of albumin passed the detector together as a single peak at a retention time of 3.1 minutes. In the myoglobin/substance P run, the myoglobin displayed a retention time of 3.1 minutes and the substance P a retention time of 3.7 minutes, which are essentially the same and in the same order as when no polymer was present in the buffer solution (Example 1A).

This result suggests that the sieve passages around the 0.25% hydroxypropyl methyl cellulose were too large to have any effect on the protein, although they might well create a sieving effect with DNA.

10% Ethylene glycol and 10% glycerin

As the monomer of PEG, ethylene glycol has similar hydrophilicity characteristics. This experiment demonstrates that, like PEG, ethylene glycol and its analog glycerin (1,2,3-propanetriol) both increase the solution viscosity, but neither produce the sieving effect attributable to PEG. Viscosity increases in themselves are therefore not responsible for the sieving effect.

Separate solutions were prepared, one containing ethylene glycol and the other glycerin, both at 10% by weight in 0.1 M pH 2.5 aqueous phosphate buffer. A third solution, containing 0.05% of the 4000-centipoise hydroxypropyl methyl cellulose solution in the same buffer, was prepared for comparison. The quantity of the latter is the amount used in the prior art for suppressing bulk flow.

Using each of the three solutions, a sample containing the albumin and fragments of substance P ranging from 4 to 11 amino acids in size was subjected to electrophoresis using the same operating column and conditions as in Example 2B. In the comparison run, the substance P fragments separated into individual peaks, but the albumin components passed the detector as a single peak at a retention time of 2.5 minutes, showing no separation between monomer, dimer and trimer. In the ethylene glycol run, all peaks passed the detector in the same order as in the control run, again with no separation of the albumin components into separate peaks. The albumin retention time was 3.4 minutes. In the glycerin run as well, all peaks passed the detector in the same order as in the control run, again with no separation of the albumin components into separate peaks. The albumin retention time was 3.5 minutes.

EXAMPLE 4

This example illustrates the separation of DNA fragments of differing lengths, using the Low Range DNA Size Standards of Bio-Rad Laboratories. The first part of this example is a control test, while the second includes the use of hydroxypropyl methyl cellulose at a concentration high enough to cause a sieving effect.

A. Electrophoresis without sieve-promoting polymer

A 3-μL sample of the mixture was electrophoretically loaded onto a 50 cm = 50μ capillary filled with a buffer solution made up of 0.089M Tris-boric acid, 0.002M ethylenediamine tetraacetic acid, and 0.1% sodium dodecyl sulfate, at a pH of 8.0.

Detection was done at 260 nm with a sensitivity range of 0.005 AUF. The DNA fragments in the sample passed the detector in three overlapping peaks at retention times of about 5-7 minutes, indicating poor if any separation of the fragments.

B. Electrophoresis with hydroxypropyl methyl cellulose in sieve-promoting amount The experiment of Part A of this example was repeated, the sole difference being that 0.5% of the 4000-centipoise hydroxypropyl methyl cellulose was additionally included in the buffer solution. The result this time was that the nine sizes of DNA fragments were well separated, with the retention times listed in Table I:

TABLE I

ELECTROPHORESIS OF DNA FRAGMENTS

| Fragment size | Retention Time |
|---|---|
| 88 base pairs | 16.2 minutes |
| 222 | 18.0 |
| 249 | 18.4 |

TABLE I-continued

ELECTROPHORESIS OF DNA FRAGMENTS

| Fragment size | Retention Time |
|---|---|
| 279 | 18.7 |
| 303 | 19.4 |
| 634 | 22.1 |
| 800 | 22.8 |
| 1434 | 24.0 |
| 1746 | 24.4 |

EXAMPLE 5

This example illustrates the separation of a mixture of at least fifteen lengths of DNA fragments, the lengths differing by 123 base pairs, beginning with 246 base pairs. Methyl cellulose was used to obtain the sieving effect.

A 3-μL sample of the mixture was electrophoretically loaded onto a 50 cm = 50μ capillary filled with a buffer solution made up of 0.089M Tris-boric acid, 0.002M ethylenediamine tetraacetic acid, and 0.5% of the 4000-centipoise methyl cellulose solution at a pH of 8.0.

Detection was done at 260 nm with a sensitivity range of 0.005 AUF. The fragments passed the detector as separate peaks, with the retention times listed in Table II:

TABLE II

ELECTROPHORESIS OF DNA FRAGMENTS

| Fragment size | Retention Time |
|---|---|
| 246 base pairs | 20.3 minutes |
| 369 | 22.2 |
| 492 | 23.8 |
| 615 | 25.3 |
| 738 | 26.4 |
| 861 | 27.2 |
| 984 | 27.7 |
| 1107 | 28.2 |
| 1230 | 28.5 |
| 1353 | 28.7 |
| 1476 | 28.9 |
| 1599 | 29.0 |
| 1722 | 29.2 |
| 1845 | 29.3 |

EXAMPLE 6

This example demonstrates the lack of effect of 1% hydroxypropyl methyl cellulose on the mobility of small ions, using a range of amounts of the polymer including amounts which are sieve-promoting in the preceding examples. The solute in this case is sodium chloride.

The polymers used in this group of tests were 15-centipoise, 50-centipoise, 100-centipoise, and 4000 centipoise hydroxypropyl methyl celluloses (HMC's). Each type of HMC was dissolved at 1% by weight in both water and a 20 mM aqueous sodium chloride solution. The conductivities of the resulting solutions were then measured and compared as indications of the effect of the polymer on the mobility of the sodium and chloride ions. The results were as listed in Table III below.

TABLE III

| | CONDUCTIVITY OF NaCl SOLUTIONS | |
|---|---|---|
| Type of HMC used (centipoise) | conductivity in water at 1% (μmhos) | conductivity in 20 mM NaCl at 1% (μmhos) |
| —* | 2.85 | 3900 |
| 15 | 140 | 4000 |
| 50 | 69 | 3900 |
| 100 | 154 | 3950 |
| 4000 | 34 | 3950 |

*Control: no polymer present.

The lack of variability of the numbers in the right column indicates that the mobility of the sodium and chloride ions is unchanged by the presence of the polymer.

EXAMPLE 7

This example is an extension of Example 2, demonstrating the effect of two additional polymer systems on the electrophoretic separation of monomer, dimer and trimer forms of bovine serum albumin.

A. Electrophoresis in the presence of dextran.

A sample solution was prepared by dissolving the monomer, dimer and trimer in 0.1M phosphate buffer at pH 2.5 to achieve a total albumin concentration of 100 μg/mL. The capillary described in Example 1 (20 cm=25μ, coated) was used, filled with the 0.1M 2.5 pH phosphate buffer further containing 10% dextran with a molecular weight of 162,000. Electrophoresis was performed by application of a potential of 8000 V, with detection at 200 nm and a sensitivity range of 0.02 AUF. The three components of the sample eluted as separate peaks, with retention times of 21.0, 23.9, and 25.8 minutes, respectively, for the monomer, dimer and trimer.

Electrophoresis in the presence of polyvinylalcohol

The separation of Part A was repeated, the only differences being the substitution of 5% polyvinylalcohol of molecular weight 50,000 for the dextran, and the use of a 35 cm =50μ capillary. The monomer, dimer and trimer again eluted as separate peaks, with retention times of 19.78, 23.92, and 26.96 minutes, respectively.

EXAMPLE 8

This example demonstrates the effect of the inclusion of dextran on the separation of bovine serum albumin, horse myoglobin and human carbonic anhydrase.

A. Electrophoresis without polymer present

The sample was prepared by dissolving the three components in 0.01M phosphate buffer at pH 2.5 to achieve concentrations of 34 μg/mL each. The capillary indicated in the preceding examples was used, filled with the 0.1M phosphate buffer at pH 2.5, and a 3 μL sample was injected, and electrophoresis performed using a potential of 10,000 V. The three components eluted as overlapping peaks, with retention times (measured at the peak vertex) of 4.7, 4.9, and 5.2 minutes, respectively, for the bovine serum albumin, horse myoglobin and human carbonic anhydrase.

B. Electrophoresis in the presence of dextran

The experiment of Part A was repeated, except that 10% dextran of molecular weight 485,000 was included in the buffer solution in the capillary. The three components eluted this time as separated peaks, with retention times (measured at the peak vertex) of 12.4, 14.5, and 18.2 minutes, respectively, for the bovine serum albumin, horse myoglobin and human carbonic anhydrase.

EXAMPLE 9

This example demonstrates the effect of two different polymer systems on the electrophoretic separation of a lactoferrin mixture consisting of the monomeric form of lactoferrin plus aggregates of various sizes. These forms are not separable by electrophoresis in the absence of these polymers, and the example illustrates that one polymer provides a significantly better separation than the other.

Electrophoresis in the presence of dextran

The sample was prepared by dissolving lactoferrin in 0.1M phosphate buffer at pH 2.5 to achieve a total lactoferrin concentration of 1 mg/mL. Electrophoresis was then performed in a 35 cm=50μ coated capillary tube filled with the same buffer solution further containing 5% dextran of 67,000 molecular weight, using a voltage of 8000 volts. All lactoferrin components emerged together as one peak.

B. Electrophoresis in the presence of polyvinylalcohol

The experiment of Part A was repeated, except that 5% polyvinylalcohol of molecular weight 50,000 was used in place of the dextran in the capillary tube. The lactoferrin components emerged this time as separate peaks, with retention times of 26.2, 31.6, and 35.6 minutes.

The foregoing is offered primarily for purposes of illustration. It will be readily apparent to those skilled in the art that modifications and variations in the procedures, materials, quantities and operating conditions described above may be made without departing from the spirit and scope of the invention.

What is claimed is:

1. A method of separating a mixture of sample ions of varying molecular weights in a sample into components, said method comprising electrophoretically passing said sample through a separation column containing a gel-free aqueous solution of a water-soluble polymer selected from the group consisting of cellulose derivatives, saccharide-based and substituted saccharide-based polymers, polysilanes, polyvinylalcohol and polyvinylpyrrolidone, said polymer having a molecular weight of about 10,000 to about 2,000,000, said molecular weight being within a range of about 0.1 to about 200 times the average molecular weight of said sample ions in said mixture, the concentration of said polymer in said solution being sufficient to retard the flow of said species through said separation column to degrees which vary with the molecular weights of said species.

2. A method in accordance with claim 1 in which said sample ions are macromolecular species, and said concentration of said polymer is sufficient to increase the retention time of said macromolecular species in said column by 25%.

3. A method in accordance with claim 1 in which said sample ions are macromolecular species, and said concentration of said polymer is sufficient to increase the retention time of said macromolecular species in said column by at least about 50%.

4. A method in accordance with claim 1 in which said polymer has an average molecular weight which is between the lowest and highest molecular weights of said sample ions in said mixture.

5. A method in accordance with claim 1 in which said polymer has a molecular weight range which is at least coextensive with that of said sample ions.

6. A method in accordance with claim 1 in which said polymer has an average molecular weight which is within a range of about 0.2 to about 20 times the average of the lowest and highest molecular weights of said sample ions.

7. A method in accordance with claim 1 in which said polymer has an average molecular weight which is within a range of about 0.5 to about 2 times the average of the lowest and highest molecular weights of said sample ions.

8. A method in accordance with claim 1 in which said separation column is a capillary tube with an internal diameter of less than about 200 microns.

9. A method in accordance with claim 1 in which said separation column is a capillary tube with an internal diameter of from about 25 microns to about 50 microns.

10. A method in accordance with claim 1 in which said separation column is a capillary tube with an internal diameter of less than about 100 microns, and the passing of said sample therethrough is achieved by applying a voltage of at least about 100 volts per centimeter of capillary tube length across said capillary tube.

11. A method in accordance with claim 1 in which said separation column is a capillary tube with an internal diameter of less than about 100 microns, and the passing of said sample therethrough is achieved by applying a voltage of at least about 300 volts per centimeter of capillary tube length across said capillary tube.

12. A method in accordance with claim 1 in which said polymer is a water-soluble cellulose derivative characterized in terms of the viscosity of a 2% aqueous solution thereof being within a range of about 15 centipoise to about 17,000 centipoise at 25° C.

13. A method in accordance with claim 1 in which said polymer is a water-soluble cellulose derivative characterized in terms of the viscosity of a 2% aqueous solution thereof being within a range of about 1,000 centipoise to about 10,000 centipoise at 25° C.

14. A method in accordance with claim 1 in which said polymer is a water-soluble cellulose derivative characterized in terms of the viscosity of a 2% aqueous solution thereof being within a range of about 1,000 centipoise to about 10,000 centipoise at 25° C., and the concentration of said polymer in said solution is at least about 0.1% by weight.

15. A method in accordance with claim 1 in which said polymer is a water-soluble cellulose derivative characterized in terms of the viscosity of a 2% aqueous solution thereof being within a range of about 1,000 centipoise to about 10,000 centipoise at 25° C., and the concentration of said polymer in said solution is from about 0.1% to about 10% by weight.

16. A method of separating a mixture of polynucleotide chains in a sample, said polynucleotide chains each containing from about 10 to about 10,000 base pairs, said method comprising electrophoretically passing said sample through a capillary column containing a gel-free aqueous solution of a substantially linear polymer selected from the group consisting of methyl cellulose, hydroxypropyl methyl cellulose, hydroxyethyl methyl cellulose, and hydroxybutyl methyl cellulose, said polymer characterized in terms of the viscosity of a 2% aqueous solution thereof being within a range of about 1,000 centipoise to about 10,000 centipoise at 25° C., and the concentration of said polymer in said solution is from about 0.1% to about 0.5% by weight.

17. A method in accordance with claim 1 in which said polymer is a member selected from the group consisting of cellulose derivatives, saccharide-based polymers, substituted saccharide-based polymers, and polyvinylalcohol.

18. A method in accordance with claim 1 in which said polymer is a member selected from the group consisting of saccharide-based polymers and substituted saccharide-based polymers.

19. A method in accordance with claim 1 in which said polymer is a polyvinylalcohol.

* * * * *